US008758998B2

(12) United States Patent
Rao

(10) Patent No.: US 8,758,998 B2
(45) Date of Patent: Jun. 24, 2014

(54) CONSTRUCTION OF BIFUNCTIONAL SHORT HAIRPIN RNA

(75) Inventor: Donald Rao, Dallas, TX (US)

(73) Assignee: Gradalis, Inc., Carrollton, TX (US)

( * ) Notice: Subject to any disclaimer, the term of this patent is extended or adjusted under 35 U.S.C. 154(b) by 66 days.

(21) Appl. No.: 13/364,053

(22) Filed: Feb. 1, 2012

(65) Prior Publication Data

US 2012/0183955 A1 Jul. 19, 2012

Related U.S. Application Data

(63) Continuation-in-part of application No. 11/983,482, filed on Nov. 9, 2007, now Pat. No. 8,252,526, which is a continuation-in-part of application No. 11/601,431, filed on Nov. 17, 2006, now Pat. No. 8,603,991.

(60) Provisional application No. 60/932,653, filed on Jun. 1, 2007, provisional application No. 60/897,214, filed on Jan. 24, 2007, provisional application No. 60/857,846, filed on Nov. 9, 2006.

(51) Int. Cl.
*C12N 15/85* (2006.01)
*A61K 48/00* (2006.01)
*C07H 21/02* (2006.01)

(52) U.S. Cl.
USPC ..... 435/6.1; 435/91.41; 435/91.51; 536/23.1; 536/24.5

(58) Field of Classification Search
USPC ............... 435/6, 91.1, 91.31, 455, 6.1, 91.41, 435/91.51; 536/23.1, 24.5
See application file for complete search history.

(56) References Cited

U.S. PATENT DOCUMENTS

| | | | |
|---|---|---|---|
| 6,506,559 | B1 | 1/2003 | Fire et al. |
| 7,615,618 | B2 | 11/2009 | Manoharan et al. |
| 7,763,722 | B2 | 7/2010 | Chang et al. |
| 2003/0138407 | A1 | 7/2003 | Lu et al. |
| 2003/0148295 | A1 | 8/2003 | Wan et al. |
| 2004/0023390 | A1 | 2/2004 | Davidson et al. |
| 2004/0213764 | A1 | 10/2004 | Wold et al. |
| 2004/0241854 | A1 | 12/2004 | Davidson et al. |
| 2005/0043263 | A1 | 2/2005 | Giese et al. |
| 2005/0080031 | A1 | 4/2005 | McSwiggen |
| 2005/0142578 | A1 | 6/2005 | Usman et al. |
| 2005/0143333 | A1 | 6/2005 | Richards et al. |
| 2009/0208514 | A1 | 8/2009 | Nakamura et al. |

FOREIGN PATENT DOCUMENTS

| | | |
|---|---|---|
| WO | 0244321 A2 | 6/2002 |
| WO | 03006477 A1 | 1/2003 |

OTHER PUBLICATIONS

Agrawal, Sudhir, et al., "Antisense Therapeutics: Is it as Simple as Complementary Base Recognition?" Molecular Medicine Today, Feb. 2000, vol. 6, 12 pages.

Ameres, Stefan Ludwig, et al., "Molecular Vasis for Target RNA Recognition and Cleavage by Human RISC," Cell, Jul. 13, 2007, pp. 101-112.
Burnett, J.C., et al., "Current Progress of siRNA/shRNA Therapeutics in Clinical Trials", Biotechnology Journal, 2011; 6:1130-1146.
Carette, Jan E., et al., "Conditionally Replicating Adenoviruses Expressing Short Hairpin RNAs Silence the Expression of a Target Gene in Cancer Cells," Cancer Research, Apr. 15, 2004, 64:2663-2667.
Chirila, Trajan V., et al., "The Use of Synthetic Polymers for Delivery of Therapeutic Antisense Oligodeoxynucleotides," Biomaterials, (2002), vol. 23, pp. 321-342.
Crooke, Stanley T., "Progress in Antisense Technology," Annu. Rev. Med., (2004), 55:61-95.
Davidson, Beverly L., et al., "Current Prospects for RNA Interference-Based Therapies," Nature Reviews Genetics, May 2011, vol. 12, pp. 329-340.
Dawson, Louise A., et al., "Design, Manufacture, and Assay for the Efficacy of siRNAs for Gene Silencing," Methods Mol Biol 2008; 439: 403-419.
Drews, Jurgen, et al., "Drug Discovery: A Historical Perspective," Science, Mar. 17, 2000, vol. 287, pp. 1960-1964.
Fire, et al., "Nobel Lectures, the Nobel Prize in Physiology or Medicine 2006," Angew. Chem. Int. Ed., (2007), 46:6966-6984.
Giering, Jeffery C., et al., "Expression of shRNA From a Tissue-Specific Pol II Promoter is an Effective and Safe RNAi Therapeutic," www.moleculartherapy.org, Sep. 2008, vol. 16, No. 9, pp. 1630-1636.
Gregory, Richard I., et al., "Human RISC Couples MicroRNA Biogenesis and Posttrranscriptional Gene Silencing," Cell, Nov. 18, 2005, vol. 123, pp. 631-640.
Grimm, Dirk, et al., "Fatality in Mice Due to Oversaturation of Cellular MicroRNA/Short Hairpin RNA Pathways," Nature, May 25, 2006, vol. 441, pp. 537-541.
Grimson, Andrew, et al., "MicroRNA Targeting Specificity in Mammals: Determinants Beyond Seed Pairing," Molecular Cell, Jul. 6, 2007, 27:91-105.
Hofacker, Ivo L., et al., "Designing Optimal siRNA Based on Target site Accessibility," Methods in MOlecular Biology, Chapter 9, (2010), pp. 137-154.
Jang, Jae-Hyung, et al., "Gene Delivery from Polymer Scaffolds for Tissue Engineering," Expert Rev. Medical Devices, (2004), 1(1):127-138.
Kim, Dong-Ho, et al., "Synthetic dsRNA Dicer Substrates Enhance RNAi Potency and Efficacy," Nature Biotechnology, Feb. 2005, vol. 23, No. 2, pp. 222-226.
Matranga, Christian, et al., "Passenger-Strand Cleavage Facilitates Assembly of siRNA into Ago2-Containing RNAi Enzyme Complexes," Cell, Nov. 15, 2005, vol. 123, pp. 607-620.

(Continued)

*Primary Examiner* — Jane Zara
(74) *Attorney, Agent, or Firm* — Edwin S. Flores; Chalker Flores, LLP

(57) ABSTRACT

A method for designing a bi-shRNA expression cassette encoding a bi-shRNA comprising: selecting one or more target site sequences; providing a backbone sequence comprising a first and a second stem-loop structure, inserting a first passenger strand and a second passenger strand and providing for synthesis of the bi-shRNA expression cassette.

31 Claims, 4 Drawing Sheets

(56) References Cited

OTHER PUBLICATIONS

Mello, CC, "Return to the RNAi World: Rethinking Gene Expression and Evolution," cell Death and Differentiation, (2007), 14:2013-2020.

Moore, Chris B., et al., "Short Hairpin RNA (shRNA): Design, Delivery, and Assessment of Gene Knockdown," Methods in Molecular Biology, Chapter 10, (2010), pp. 139-156.

Opalinska, Joanna B., et al., "Nucleic-Acid Therapeutics: Basic Principles and Recent Applications," Nature Reviews, Jul. 2002, vol. 1, pp. 503-514.

Paroo, Zain, et al., "Challenges for RNAi in vivo," Trends in Biotechnology, Aug. 2004, vol. 22, No. 8, pp. 390-394.

Peracchi, Alessio, "Prospects for Antiviral Ribozymes and Deoxyribozymes," Rev. Med. Virol., (2004), 14:47-64.

Petricoin, Emanuel F., et al., "Clinical Proteomics: Translating Benchside Promise into Bedside Reality," Nature Reviews—Drug Discovery, Sep. 2002, vol. 1, pp. 683-695.

Phalon, Connor, et al., "Potential Use of RNA Interference in Cancer Therapy," Expert Reviews in Molecular Medicine, Aug. 2010, vol. 12, 16 pages.

Preall, Jonathan B., et al., "RNAi: RISC Gets Loaded," Cell, Nov. 18, 2005, vol. 123, pp. 543-553.

Rao, Donald D., et al., "siRNA vs. shRNA: Similarities and Differences," Advanced Drug Delivery Reviews, (2009), 61:746-759.

Rao, DD., et al., "Enhanced Target Gene Knockdown by a Bifunctional shRNA: A Novel Approach of RNA Interference," Cancer Gene Therapy, (2010), pp. 1-12.

Shen, Yuqiao, et al., Individualised Cancer Therapeutics: Dream or Reality? Therapeutics Construction, Expert Opin. Biol. Ther., (2005) 5(11):1427-1441.

Simari, Robert D., et al., "Requirements for Enhanced Transgene Expression by Untranslated Sequences from the Human Cytomegalovirus Immediate-Early Gene," Molecular Medicine, (1998), 4:700-706.

Siolas, Despina, et al., "Synthetic shRNAs as Potent RNAi Triggers," Nature Biotechnoloty, Feb. 2005, vol. 23, No. 2, pp. 227-231.

Templeton, Nancy Smyth, et al., "Improved DNA: Liposome Complexes for Increased Systemic Delivery and Gene Expression," Nature Biotechnology, vol. 15, Jul. 1997, pp. 647-652.

Verdine, Gregory L., et al., "The Challenge of Drugging Undruggable Targets in Cancer: Lessons Learned from Targeting BCL-2 Family Members," Clinical Cancer Res., (2007), 13:7264-7270.

Walton, S. Patrick, et al., "Designing Highly Active siRNAs for Therapeutic Applications," FEBS Journal, (2010) 277:4806-4813.

Wang, Zhachui, et al., "RNA Interference and Cancer Therapy," Pharm. Red., Apr. 20, 2011, 13 pages.

Welsh, John B., et al., "Analysis of Gene Expression Profiles in Normal and Neoplastic Ovarian Tissue Samples Identifies Candidate Molecular Markers of Epithelial Ovarian Cancer," PNAS, Jan. 30, 2001, vol. 98, No. 3, pp. 1176-1181.

SEQUENCE LISTING

<160> NUMBER OF SEQ ID NOS: 6

<210> SEQ ID NO 1
<211> LENGTH: 17
<212> TYPE: RNA
<213> ORGANISM: artificial sequence
<220> FEATURE:
<223> OTHER INFORMATION: synthetic oligonucleotide

<400> SEQUENCE: 1
agugaagcca cagaugu                                                    17

<210> SEQ ID NO 2
<211> LENGTH: 17
<212> TYPE: RNA
<213> ORGANISM: artificial sequence
<220> FEATURE:
<223> OTHER INFORMATION: synthetic oligonucleotide

<400> SEQUENCE: 2
agugaagcca cagaugu                                                    17

<210> SEQ ID NO 3
<211> LENGTH: 15
<212> TYPE: RNA
<213> ORGANISM: artificial sequence
<220> FEATURE:
<223> OTHER INFORMATION: synthetic oligonucleotide

<400> SEQUENCE: 3
uugacaguga gcgcc                                                      15

<210> SEQ ID NO 4
<211> LENGTH: 17
<212> TYPE: RNA
<213> ORGANISM: artificial sequence
<220> FEATURE:
<223> OTHER INFORMATION: synthetic oligonucleotide

<400> SEQUENCE: 4
guugccuacu gccucgg                                                    17

```
<210> SEQ ID NO 5
<211> LENGTH: 19
<212> TYPE: RNA
<213> ORGANISM: artificial sequence
<220> FEATURE:
<223> OTHER INFORMATION: synthetic oligonucleotide

<400> SEQUENCE: 5
gcuguugaca gugagcgcc                                                   19

<210> SEQ ID NO 6
<211> LENGTH: 21
<212> TYPE: RNA
<213> ORGANISM: artificial sequence
<220> FEATURE:
<223> OTHER INFORMATION: synthetic oligonucleotide

<400> SEQUENCE: 6
guugccuacu gccucggaag c                                                21
```

US 8,758,998 B2

CONSTRUCTION OF BIFUNCTIONAL SHORT HAIRPIN RNA

CROSS-REFERENCE TO RELATED APPLICATIONS

This patent application is a continuation-in-part of, claims priority to, and incorporates by reference U.S. patent application Ser. No. 11/983,482, filed on Nov. 9, 2007 and 11/601,431, filed Nov. 17, 2006. This patent application further claims priority to, and incorporates by reference, U.S. provisional patent application Ser. No. 60/932,653, filed Jun. 1, 2007; Ser. No. 60/897,214, filed Jan. 24, 2007; and Ser. No. 60/857,846, filed Nov. 9, 2006. The entire contents of these applications are incorporated herein by reference.

TECHNICAL FIELD OF THE INVENTION

The present invention relates in general to certain novel shRNA molecules and methods of creating, designing, preparing, constructing, and using thereof. Provided are bi-functional short hairpin RNA (bi-shRNA) technologies with enhanced potency.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with artificial double-stranded small interfering RNAs (siRNAs) as well as introduction thereof into animal and plant cells, which the inventor recognize to induce degradation of targeted mRNA molecules with homologous sequences. The use of siRNAs in such manner is a type of process that is generally known as RNA interference (RNAi). RNAi has emerged as a useful experimental tool with strong potential for therapeutic applications. However, in mammalian cells, induction of RNAi requires the transfection of RNA oligonucleotides, which can be inefficient and often gives rise to only a transient inhibition of target gene expression.

The discovery of RNA interference (RNAi) engendered great excitement and raised expectations regarding its potential applications in biomedical research and clinical application. Over the ensuing years, expanded understanding of RNAi and preliminary results from early clinical trials tempered enthusiasm with realistic appraisal resulting in cautious optimism and a better understanding of necessary research and clinical directions.

One type of RNAi involves the use of short hairpin RNAs (shRNAs). shRNAs consist of a stem-loop structure that can be transcribed in cells from an RNA polymerase II or RNA polymerase III promoter on a plasmid construct. It has been shown that expression of shRNA from a plasmid can be stably integrated for constitutive expression, which may provide certain advantages over synthetic siRNA. shRNAs, as opposed to siRNAs, are synthesized in the nucleus of cells, further processed and transported to the cytoplasm, and then incorporated into the RNA-induced silencing complex (RISC) for activity.

The Argonaute family of proteins is the major component of RISC. Within the Argonaute family of proteins, only Ago2 contains endonuclease activity that is capable of cleaving and releasing the passenger strand from the stem portion of the shRNA molecule. The remaining three members of Argonaute family, Ago1, Ago3 and Ago4, which do not have identifiable endonuclease activity, are also assembled into RISC facilitated by a non-endonuclease mediated unwinding of the passenger strand from the stem portion of the si/shRNA molecule. Consequently, guide strand loading onto RISC is by way of either cleavage-dependent or cleavage-independent "loading pathways".

Ago2 containing RISC initiates target mRNA degradation through a cleavage-dependent effector pathway whereas other three Agos containing RISCs partially-complementary to mRNA inhibit target mRNA function through a cleavage-independent effector pathway. Thus, RISC can be characterized as having cleavage-dependent and cleavage-independent "effector pathways".

The recently discovered micro-RNA (miRNA) is a new class of endogenous RNA interference molecule that is synthesized in the nucleus, one component of which is a pre-miRNA, a structure emulated by shRNA. This new class of short, single-stranded miRNAs are found both in plant and animal cells and are derived from larger precursors that form a predicted RNA stem-loop structure. These miRNA precursor molecules are transcribed from autonomous promoters—or are instead contained within longer RNAs. More than 1700 distinct human miRNAs have been discovered to date, some of which are expressed in organisms as diverse as nematodes. miRNAs appear to play a role in the regulation of gene expression, primarily at the post-transcriptional level via translation repression. Several miRNAs have been shown to be evolutionarily conserved from *C. elegans* to man.

Like mRNAs, miRNAs are initially transcribed by RNA polymerase II into a long primary transcript (pri-miRNA) that contains one or more hairpin-like stem-loop shRNA structures. The stem-loop shRNA structures within the pri-miRNA are further processed in the nucleus by the RNase III enzyme Drosha and its cofactor DGCR-8 into pre-miRNA. Pre-miRNA is transported to the cytoplasm by the transport receptor complex Exportin-5-RanGTP, where it interacts with a second RNase III enzyme Dicer and its cofactor TRBP. Dicer trims off the loop and presents the remaining double stranded stem to the RISC for loading; subsequently, the passenger strand of the double stranded stem on the RISC departs for the guide strand containing RISC to seek-out target mRNA for down regulation.

While siRNAs, shRNAs, and miRNAs have been used to suppress the expression of certain target genes with moderate success, a need exists for improved versions of RNAi molecules. Preferably, such RNAi molecules will exhibit an improved ability to suppress the expression level of target genes (i.e., improved efficacy) and, furthermore, will be capable of suppressing gene expression over a longer period of time.

SUMMARY OF THE INVENTION

Without limiting the scope of the invention, its background is described in connection with methods for designing bi-shRNA expression cassettes encoding bi-shRNAs comprising selecting one or more first target site sequences of a targeted species, wherein the one or more first target site sequences have low homology with other mRNAs of the targeted species, wherein low homology is selected from the group consisting of less then 75%, less then 80%, less then 90%, less then 95%, and less then 98%; homology. The method further comprises selecting one or more second target site sequences of a targeted species, wherein the one or more first target site sequences have low homology with other mRNAs of the targeted species, wherein low homology is selected from the group consisting of less then 75%, less then 80%, less then 90%, less then 95%, and less then 98%; homology; providing a backbone sequence comprising a first and a second stem-loop structure, wherein the first stem-loop structure comprises two first insertion sites linked by a first loop sequence within the first stem and wherein the second stem-loop structure comprises two second insertion sites linked by a second loop sequence within the second stem; inserting a first passenger strand and a first guide strand into the two first insertion sites to form the first stem, wherein the first passenger strand is homologous to the one or more first target site sequences and wherein the first guide strand is complementary to the first passenger strand, or wherein the first passenger strand is identical to the reverse orientation of the first guide strand; inserting a second passenger strand and a second guide strand into the two second insertion sites to form the second stem-loop structure, wherein either the second passenger strand or the second guide strand is homologous with the one or more second target sites sequences, wherein the second passenger strand and the second guide strand are partially complementary, wherein partially complementary is defined has having 1, 1-2, 1-3, 1-4, 1-5, 1-6, 1-7, 1-8, 1-9, or 1-10 nucleotide mismatches when paired. In one aspect, the method also includes the step of providing for synthesis of the bi-shRNA expression cassette. In another aspect, the targeted species is selected from a human, a plant or an animal nucleic acid sequence. In one aspect, the first stem-loop structure and the second stem-loop structure each comprise a loop of 6-15 nucleotides in size. The first stem-loop structure and the second stem-loop structure may also each 40 to 100 nucleotides long. The first stem-loop structure and the second stem-loop structure may also each 50 to 75 nucleotides long. In one aspect, the first stem-loop structure and the second stem-loop structure each comprise a stem of 19-45 nucleotides in size, or the first stem-loop structure and the second stem-loop structure may each comprise a stem of 20-30 nucleotides in size. At least one passenger strand and one guide strand may be 16-19 nucleotides long, or 19-22 nucleotides long. The first loop and the second loop may also be identical. The first loop may encode the sequence AGUGAAGCCACAGAUGU (SEQ ID NO.:1). The second loop may encode the sequence AGUGAAGCCA-CAGAUGU (SEQ ID NO.:2). The backbone sequence may comprises the following sequence upstream of the first passenger strand and within the first stem: UUGA-CAGUGAGCGCC (SEQ ID NO.:3); and the backbone sequence may comprise the following sequence downstream of the first guide strand and within the first stem: GUUGC-CUACUGCCUCGG (SEQ ID NO.:4). In one aspect, the backbone sequence comprises the following sequence upstream of the second passenger strand and within the second stem: GCUGUUGACAGUGAGCGCC (SEQ ID NO.: 5); the backbone sequence may comprises the following sequence downstream of the second guide strand and within the second stem: GUUGCCUACUGCCUCGGAAGC (SEQ ID NO.:6). In one aspect, the one or more nucleotide mismatches may be located at nucleotide position 9, 10, and 11. In one embodiment, the method may comprise determining a ΔG free energy of the second stem loop structure and introducing additional mismatches at the 3' half of the second passenger strand if ΔG free energy is beyond about −10 Kcal-.mole-1. The bi-shRNA expression cassette may further comprise a lead transcript upstream of the stem-loop structures, wherein the lead transcript is characterized in that it is at least 30 nucleotides or longer in lengths and does not interfere with transcription of the bi-shRNA expression cassette. In one aspect, the method of claim 1, may comprise at least three bi-shRNA expression cassettes for the same gene; and comparing knockdown efficiency of the at least three bi-shRNA expression cassettes by in vitro assessment. In one aspect, the method may comprise operably linking the bi-shRNA expression cassette to a promoter, wherein the second stem-loop structure is upstream in relation to the first stem loop structure, or wherein the first stem-loop structure is upstream in relation to the second stem loop structure.

In addition, the method may comprise integrating the bi-shRNA expression cassette into genomic DNA, wherein the genomic DNA is selected from the group comprising animal DNA, insect DNA, plant DNA, algae DNA, fungus DNA, yeast DNA, bacteria DNA, and human DNA. In one aspect, the method may further comprise inserting the bi-shRNA expression cassette into an expression vector. The expression vector may comprise a 5'UTR and an intron. In one aspect, the expression vector may comprise a RNA polymerase II promoter operably linked to the expression of the bi-shRNA expression cassette. The backbone sequence may comprise a miR30a backbone sequence. Selecting one or more target site sequences may comprise searching by BLAST to find target sites with lowest homology hits to other mRNA of the targeted species. Providing for synthesis may be selected from the group comprising assembling multiple overlapping DNA oligonucleotides, synthesizing a polynucleotide, and combinations thereof. In addition, providing for synthesis may comprise designing DNA oligonucleotides from both strands having an overlap, wherein the overlap is at least four nucleotides. In one aspect, the method may comprise preparing a DNA-DOTAP:Chol Lipoplex. In one aspect, the one or more first target site sequences are identical to the second one or more target site sequences. In one aspect, the one or more first target site sequences and the one or more second target site sequence are homolog to a sequence located within the same transcript of the targeted species. In one additional aspect, the one or more first target site sequences and the one or more second target site sequence are homolog to a sequence located within the same gene of the targeted species. Another embodiment is a bifunctional shRNA made by the methods described herein.

BRIEF DESCRIPTION OF THE DRAWINGS

For a more complete understanding of the features and advantages of the present invention, reference is now made to the detailed description of the invention along with the accompanying figures and in which:

FIG. 2(a) provides an example of an embodiment of a predicted RNA structure of the bi-shRNA in the miR30a backbone. Two stem-loop structures are juxtaposed to each other each with the identical guide strand (light purple); the first one completely complementary to the passenger strand (light blue box), the second one with a mismatched passenger strand (light blue box). FIG. 2(b) shows a schematic representation of the assembly process with overlapping fragments to generate the bi-shRNA expression unit. Overlapping fragments cover the entire expression unit. The fragments are designed with sticky ends to facilitate joining by ligation. The assembly process proceeds in stepwise fashion. The 5' end fragments (orange) are ligated together. The 3' fragments are ligated together (black and purple) before being joined together with the middle fragment (green).

FIG. 3(a) schematically depicts the stem-loop RT-PCR procedure. A stem-loop RT primer is designed with at least a 4-base overhang at the 3' end to recognize the 3' end of siRNA/mature miRNA (shRNA). After RT, PCR amplification is accomplished with a siRNA/mature miRNA (shRNA) specific PCR primer and stem-loop RT primer specific PCR primer. FIG. 3(b) shows a typical result of stem-loop RT-PCR. PCR products that were run onto a 3% agarose gel. Lane (a) is a 10 bp size marker, (b) is a control with cellular RNA isolated from untransfected cells, (c) is a control with cellular RNA isolated from cells transfected with scrambled siRNA, (d) is with cellular RNA isolated from cells transfected with bi-shRNA, (e) is with cellular RNA isolated from cells transfected with siRNA, and (f) is RNA isolated from bi-shRNA transfeced cells without RT reaction.

FIG. 4(a) schematically depicts a 5'RLM-RACE method. Cleaved or partially degraded mRNA with exposed 5' ends are first ligated with an RNA oligo via RNA ligase. The RNA oligo added RNA fragment is selectively copied into cDNA with gene specific primer, and the cDNA is further amplified by nested gene specific primer and RNA oligo specific primer. FIG. 4(b) shows a typical result of 5'RLM-RACE. PCR products were run onto a 1.5% agarose gel. Lane (a) is a 100 bp size marker, (b) is a control with cellular RNA isolated from untransfected cells, (c) is a control with cellular RNA isolated from cells transfected with scramble siRNA, (d) is with cellular RNA isolated from cells transfected with bi-shRNA, (e) is with cellular RNA isolated from cells transfected with siRNA, and (f) is RNA isolated from bi-shRNA transfected cells without RT reaction.

DETAILED DESCRIPTION OF THE INVENTION

Figure 1:
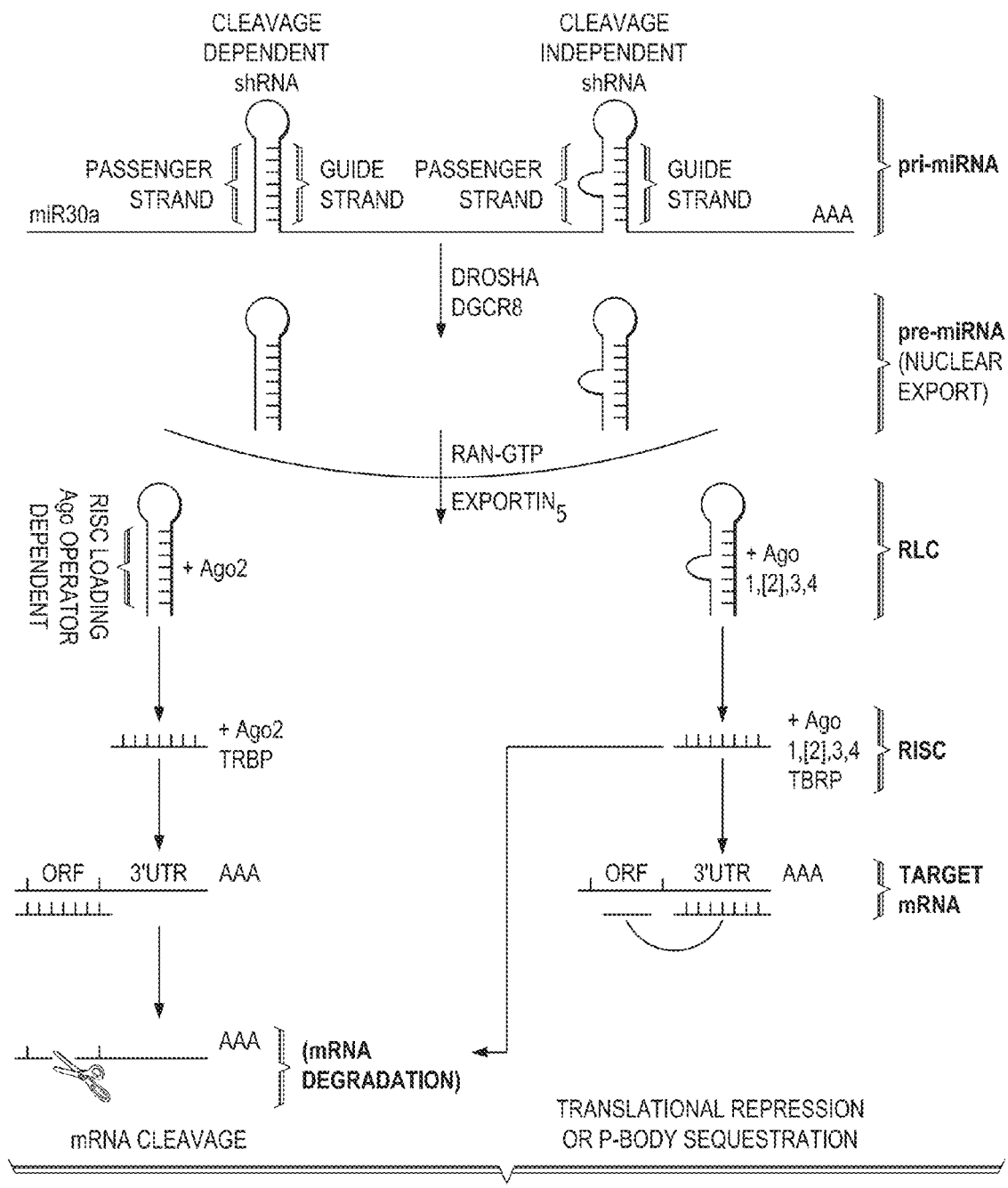
FIG. 1 shows the principle of bi-functional shRNA. Like a significant percentage of intronic miRNA, the primary transcripts of bi-shRNA are first synthesized in the nucleus by RNA polymerase II. The primary transcripts are quickly processed by the microprocessor, primarily consisting of Drosha and DGCR8, into individual stem-loop structures. The stem-loop structures are exported from the nucleus to the cytoplasm via Exportin 5 and/or Exportin 1 (CRM1), where upon association with Dicer and RISC loading complex (RLC), the loop of the stem-loop structures are removed. Upon loading onto multiple types of Ago containing RISC, the passenger strands of bi-shRNA depart through a cleavage-dependent and a cleavage-independent loading process so that the guide strands are effectively programmatically loaded onto multiple types of Ago containing RISC to more efficiently execute RNAi through either mRNA cleavage and degradation or through translational repression, p-body sequestration and degradation (cleavage-dependent or cleavage-independent effector pathways, respectively) the guide strands of each of which are complementary to the target mRNA in this configuration.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present inventor recognize that the capability of delivering a pharmacologically effective dose to the target site while avoiding adverse host reactions still remained a challenge although the delivery technology continues to improve. The present inventor has developed a novel vector driven bi-functional short hairpin RNA (bi-shRNA) technology with enhanced potency. Advantages provided by the enhanced potency bi-shRNA include lower active systemic doses to further limit off-target side effects and a more durable effective dose for clinical applications. Here, key molecular methods useful for utilizing this technology are provided.

RNA interference (RNAi), the Nobel prize winning discovery by Fire and Mello in 1998, has fostered an exponential number of studies and publications furthering the understanding of gene function (1, 2) and stimulating numerous phase I and II clinical trials (3-6). This naturally occurring gene-silencing mechanism by small RNAs, which includes endogenous microRNA (miRNA), is highly dependent on gene sequence; thus the mechanism can, in theory, be used to inhibit the expression of any targeted gene[s] with strong specificity. RNAi is not limited by the pharmacologic constraints inherent to the development of small molecules which creates an opportunity to access traditionally "undruggable" targets for disease treatment (7-9).

The central player of this mechanism is the RNA Induced Silencing Complex (RISC). The process starts with double-stranded small RNA (composed of a passenger strand and a guide strand) which is incorporated into the pre-RISC followed by the cleavage-dependent or cleavage-independent release of the passenger strand to form the guide strand containing RISC (10). The guide strand (anti-sense to mRNA) guides the RISC to recognize the target mRNA through sequence complementarity (full or extended partial) (11). A key component of RISC is the family of Argonaute proteins (Ago), Ago 1, 2, 3 and 4 in mammalian systems, of which only Ago 2 has endonuclease activity so as to allow for cleavage of the target mRNA for further degradation (cleavage dependent pathway) (10, 12); all the Ago containing RISC can function through a cleavage-independent effector pathway resulting in translation repression and mRNA sequestration in p-body with subsequent degradation (13, 14). The cleavage-dependent effector process requires extensive homology between guide strand and both the passenger strand and target mRNA, particularly in the central region; the cleavage-independent effector process, on the other hand, only requires partial homology between guide strand and both the passenger strand and target mRNA (15-17).

The present invention takes advantage of both cleavage dependent and cleavage independent loading at the RISC complex, not downstream from the RISC complex. Thus, as used herein the phrase "cleavage dependent and cleavage independent" refers to the design of RNA(s) that are specifically targeted to RISC and the cleavage dependent and cleavage independent activities at the RISC complex, i.e. loading. It has been found herein and in the parent application for this case, that these "bifunctional shRNAs" have a higher inhibitory activity than the sum of targeting each individual part of the RISC complex. Thus, the higher inhibitory activity of the present invention.

RNA interference can be triggered either by synthetic double stranded small interfering RNA (siRNA) or by vector driven short hairpin RNA (shRNA) (5, 18). Both siRNA and vector driven shRNA have been demonstrated to be effective in in vitro and in vivo applications, each with their respective advantages. Most siRNA are structurally designed to promote efficient incorporation into the Ago2 containing RISC, the RNase III containing Dicer-substrate design improves the efficiency of siRNA at least 10-fold by initial association and processing at the pre-RISC (19). Vector driven shRNA utilizes the host microRNA biogenesis pathway, which appears to be more efficient (20, 21). siRNA is more readily chemically modified while shRNA expression can be modulated and regulated by specific promoters.

The present inventors developed the novel vector driven shRNA technology, the bi-functional shRNA (bi-shRNA), to further improve the efficiency of RNAi by harnessing both cleavage-dependent and cleavage-independent pathways of RISC loading in one pre-programed molecule (FIG. 1) (18, 21). The vector driven bi-shRNA includes two stem-loop structures for each mRNA target sequence, one stem-loop shRNA has perfect complementarity at the stem and the second stem-loop shRNA contains mismatches on the passenger strand of the stem (thereby differing from prior art mismatched RNA that include the mismatch on the guide strand). Importantly, following incorporation into the RISC, the guide strands derived from each of the two structures are fully complementary to the mRNA target sequence but are associated with different Ago containing RISCs. The bi-shRNA design leads to more rapid onset of gene silencing, higher efficacy, and greater durability when compared with either siRNA or conventional shRNA (21). Currently personalized cancer therapy with target specific bi-shRNA is transitioned into the clinic in Phase I studies using a modified bilamellar invaginated liposome delivery vehicle (22). Key molecular methods involved in design, construction, and the implementation of bi-shRNA are provided below.

Briefly, a target gene is selected, and in certain embodiments, an initial step is to determine the objective of the study. Depending on that objective and the embodiments, several different vectors, promoters, or plasmid backbones and delivery systems can be used. It has been found useful to choose an expression vector with efficient transgene expression. The inventor found that an expression vector with powerful promoters, e.g., an extended CMV promoter containing IE 5'UTR and partial Intron A (pUMVC3), is more effective than those with a cloning site immediately adjacent to the CMV promoter (23, 24). In certain embodiments it is beneficial to have a stretch of lead transcript before the stem-loop structures. In addition, if more than one vector usage is planned, an effective shuttle strategy should be worked out beforehand; modification by PCR amplification of the expressed cassette is not as efficient. The choice of promoter is also important; RNA polymerase III promoters are much stronger in expression but competitively saturate the endogenous miRNA maturation process at both the nuclear export and RISC loading steps resulting in lethal toxicity in vitro and in vivo with certain delivery vehicles (25). RNA polymerase II promoters, although less strong in expression, works efficiently and is much less toxic vis-à-vis competition for the endogenous miRNA pathway (26).

In certain embodiments a sequence that can act in more than one species is designed, particularly if multiple animal model systems are utilized. For most target genes, it is possible to find stretches of target nucleotides that are conserved between species. For finding a sequence that is both conserved and optimum for knockdown, one has to compare the homology-matched sequence with the selected target site sequence.

Public accessible computer programs using differing algorithms (e.g. Dharmacon RNAi design center (www.dharmacon.com) and IDT (www.idtdna.com) are readily available and can be used to locate appropriate target sites within the targeted gene. A search with most computer programs will often yield a preliminary first set of targets for further analysis. Some available publications offer do and do-not suggestions (27-30). A BLAST search for each target sequence is to be taken in order to analyze potential cross homology with other mRNAs within the species of interest.

Figure 2A:
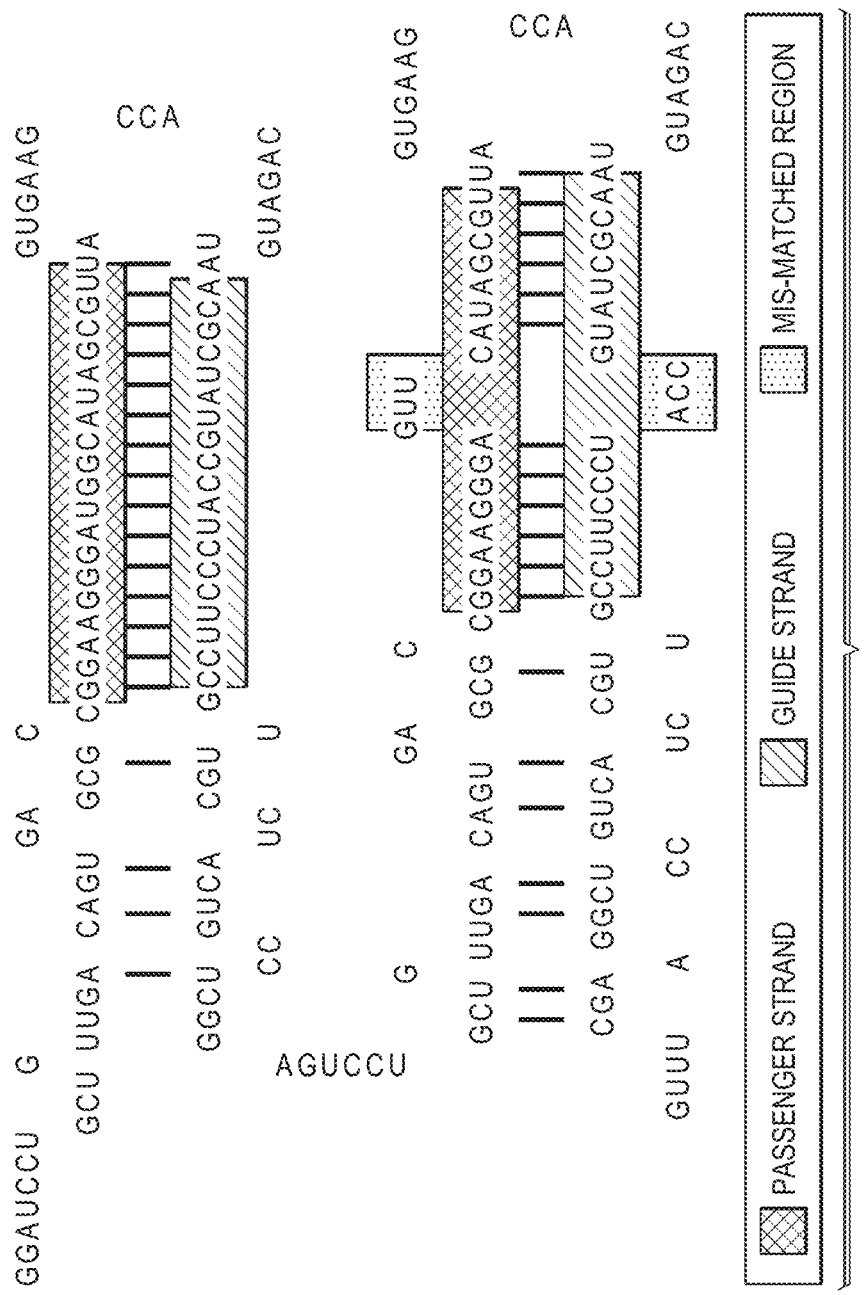
FIGS. 2(a) and 2(b) illustrate bi-shRNA structure and the construction assembly process.

Once the target site sequence is selected, the bi-shRNA design process can begin; the design process is presented below. The bi-shRNA stem-loop structure routinely used by the inventor employs the well-analyzed miR-30a backbone (31, 32), although, any functional miRNA backbone can be used. An example of a predicted stem-loop structure of a bi-functional construct is shown in FIG. 2(a). The bi-shRNA consists of the two stem-loop structures on a miR-30a backbone located immediately adjacent to each other with a gap about 10 nucleotides long. See FIG. 2(a). A longer nucleotide gap can be used and multiple units of bi-sh RNA can be designed to string together in a single transcript targeting either a single gene at multiple sites or multiple different genes simultaneously.

Figure 2B:
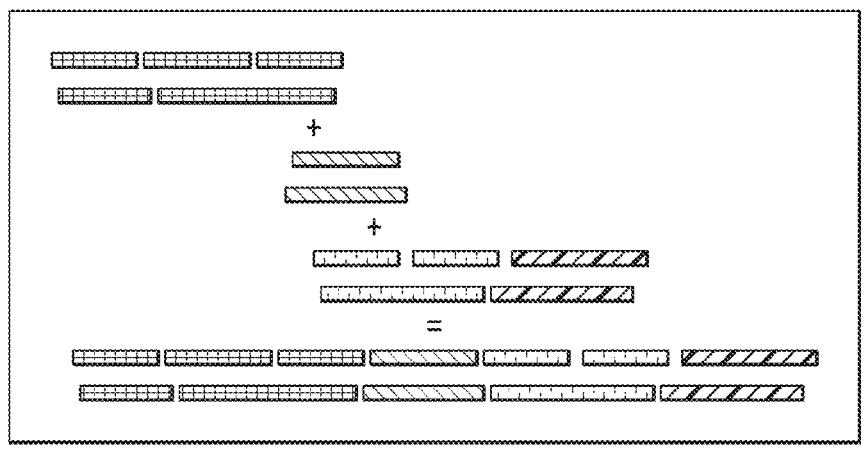

To construct the expression unit to be placed in the multiple cloning sites of an expression vector, an assembly strategy using synthetic oligonucleotides sequentially linked together has been developed. See FIG. 2(b). Alternatively, one can also outsource the synthesis of the gene construct with the specified sequence to a biotechnology service company. For the oligonucleotide assembly process, overlapping DNA fragments were designed and synthesized. Because of redundant sequences in the two stem-loop structures, it is necessary to initially ligate the 5' fragments and 3' fragments. The 5' fragment and the 3' fragment can then be purified on gel and further ligated to the middle linking fragments as illustrated on FIG. 2(b) and described below. This assembly process is efficient and, with careful design, many fragments can be repetitively used for different bi-functional constructs.

For each target, it is the best to design and construct at least three bi-functional constructs to compare and from which to select a construct with high knockdown efficiency for further evaluation. Knockdown efficiency can be compared in vitro in tissue culture cells. The inventor has recognized that is generally difficult to compare the knockdown efficiency with endogenously expressed genes because in vitro transfection methods have widely different efficiencies; this is particularly so when the transfection efficiency is low as the knockdown is hard to assess due to background noise from untransfected cells. The present inventor has developed a more effective method in which both the bi-functional construct and transgene expression vector are co-transfected; this allows target gene expression knockdown to be effectively compared and quantified.

Figure 3A:
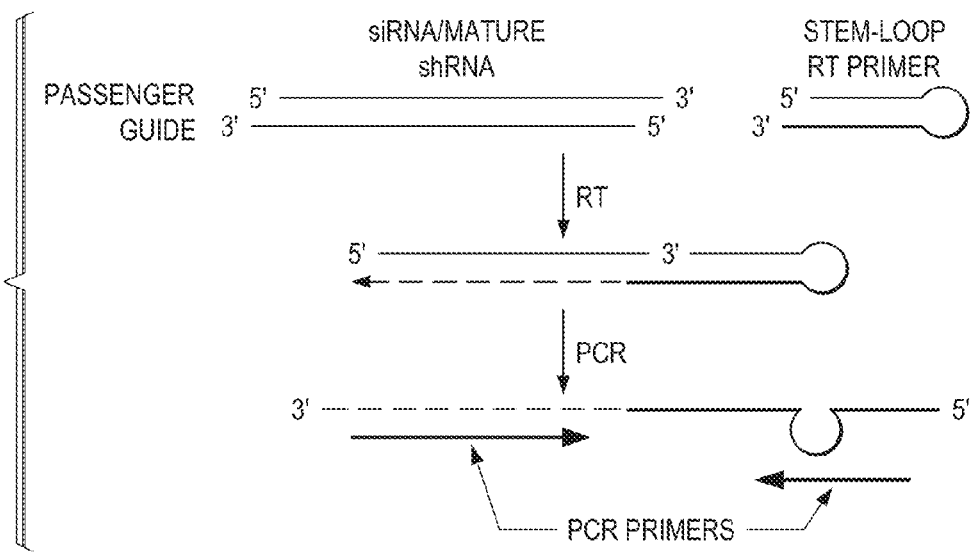
FIGS. 3(a) and 3(b) illustrate and document stem-loop RT-PCR to detect mature shRNAs.
Figure 3B:
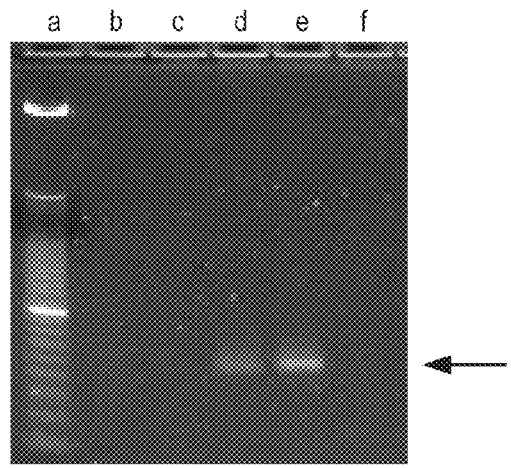
Figure 4A:
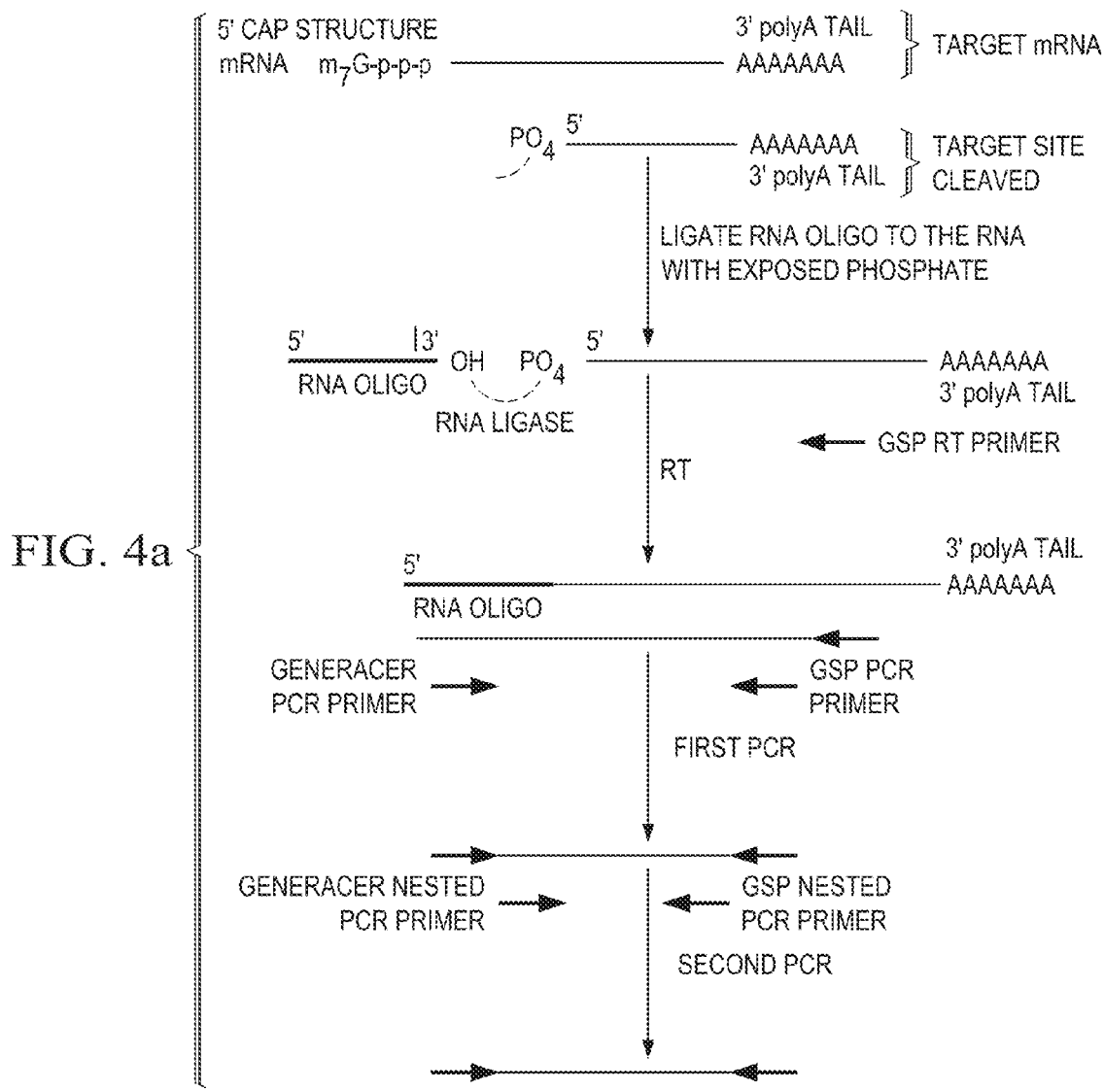
FIGS. 4(a) and 4(b) illustrate and document 5' RNA-ligand mediated RACE (5'RLM-RACE) to detect target site cleavage product.
Figure 4B:
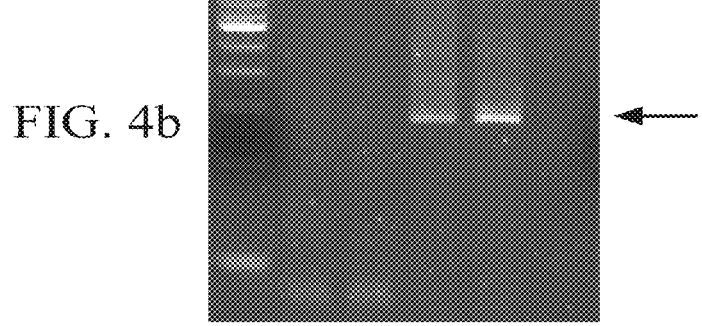

Efficacy and efficiency of target gene knockdown by bi-shRNA can be tested with a variety of in vitro and in vivo systems depending on the target and planned application. This in vitro assessment can be conducted following transfection of the bi-shRNA expression plasmids in a variety of cultured cells. The present inventor found that transfections by both electroporation and by liposome (e.g. Lipofectamine 2000) are highly effective, when the amount of plasmid DNA is carefully controlled using a control vector or universal random sequence. For Lipofectamine or a related agent, the present inventor found that the reverse transfection method, in general, is less toxic than the forward transfection method. Target gene knockdown can be assessed by either qRT-PCR for target gene mRNA or by Western and/or ELISA for target gene protein. These assays are well described in many publications. Two assay methods are presented in detail here: one detects the expression of mature shRNA by stem-loop RT-PCR, the other detects the target mRNA cleavage by 5' RNA-Ligand Mediated RACE (5' RLM-RACE). Both these methods were successfully used to assess the efficacy of bi-shRNA both in vitro and in vivo. The stem-loop RT-PCR method is schematically illustrated in FIG. 3(a) and a typical result shown in FIG. 3(b). Stem-loop RT-PCR is a sensitive method dependent on the specific probe primer used; in addition, one can specifically detect and quantify both the passenger strand and guide strand. For bi-shRNA, the method can differentially score both the fully complementary as well as the mismatched (partially complementary) passenger strand (21). The 5' RLM-RACE method is schematically shown in FIG. 4(a); the method requires ligation of an RNA oligomer onto the cleaved mRNA end, consequently, the method is rendered less efficient. Insofar as a number of rounds of amplifications are often required, a nested primer design is essential to ensure specificity. A typical result is shown in FIG. 4(b).

Evaluable functionality of bi-shRNA relies on effective plasmid delivery into target cells. The inventors recognize that some in vitro transfection systems often do not translate to inherently more complex in vivo animal models (33). There are numerous delivery systems designed specifically for systemic applications in vivo (22, 33-35). The present inventor has utilized the fusogenic, cationic DOTAP:cholesterol bilamellar invaginated vesicle lipoplex (BIV) for in vivo studies (22, 36) and has successfully translated it to the clinic (37). Currently modification strategies for more focused biodistribution, targeted delivery, and enhanced intracellular uptake are being developed. An effective lipoplex should use plasmids devoid of any contaminants from host E. coli. Although endo-free plasmid purification kit produced plasmids are generally used, GLP or GMP produced plasmids are more effective. Unfortunately, colanic acid and other non-endotoxin associated polysaccharides co-purify with DNA by anion exchange chromatography and by cesium chloride density gradient centrifugation. Therefore, endotoxin removal does not remove these contaminants, and HPLC cannot detect these contaminants. To correct this, the Superclean™ procedure has been developed to generate ultra-high quality plasmid DNA, cleansed of these contaminants, for in vivo and clinical applications (38). Liposome preparation involves highly specialized equipment; the present inventors routinely generate the DOTAP:cholesterol BIV in a GMP facility. Pre-made liposome may be obtained from a collaborator or purchased from a vendor. The process of preparing lipoplex with high quality liposome and plasmid DNA is described below. The lipoplex formulation can be achieved in most laboratory settings. Once the lipoplex is made, the formulation can be delivered systemically to experimental animals either through slow tail vein injection or with catheters. Target site vector expression can be analyzed using the PCR method for plasmid DNA and the stem-loop RT-PCR for mature bi-shRNA, respectively. bi-shRNA functionality can be assayed with the 5' RLM-RACE for target mRNA cleavage and with Western blot or IHC for target protein knockdown. These analyses can be performed at about 48 hours post treatment. For efficacy, repeated delivery into the experimental animal is often required; the dosing schedule needs to be experimentally determined and optimized.

The invention provides that target gene-specific shRNAs may be designed to enter into and interact with the cleavage-dependent RISC and cleavage-independent RISC pathways. As used herein, the term "bifunctional shRNA" generally means one or more RNA molecules, each of which include a double stranded sequence that resides within a stem portion of separate stem-loop structures, wherein a first RNA molecule is designed to be presented to a cleavage-dependent RISC pathway and a second RNA molecule is designed to be presented to a cleavage-independent RISC pathway. In certain embodiments, the bi-shRNA is all on a single strand.

More specifically, a first guide strand sequence is complementary, preferably 100% complementary, to at least a portion of an mRNA transcript encoded by a target gene. The invention provides that this guide strand (which is initially bonded to the passenger strand to form the double stranded stem) comprises a nucleic acid sequence that is capable of binding to the mRNA transcript of the target gene, and is presented to the cleavage-dependent RISC pathway. The invention provides that such binding of the guide strand sequence to the mRNA transcript, and presentation to the cleavage-dependent RISC pathway, causes degradation of the mRNA transcript.

In particular embodiments, it is provided that the second guide strand sequence is at least partially complementary to at least a portion of the mRNA transcript encoded by the target gene. More particularly, the second guide strand sequence may contain a first portion that is complementary, preferably 100% complementary, to the mRNA transcript encoded by the target gene, whereas a second portion of the guide strand sequence contains certain bases that are mismatched with the corresponding sequence of the target gene mRNA transcript.

As used herein, a "mismatched" base pair refers to two nitrogenous bases within a nucleic acid sequence that, when bound (or hybridized) to each other, do not follow Chargaff's rules of base pairing. Chargaff's rules provide that the purine adenine (A) within a first nucleic acid sequence will pair with the pyrimidine thymine (T) (or uridine (U)) within a second nucleic acid sequence. Furthermore, Chargaff's rules provide that the purine guanine (G) within a first nucleic acid sequence will pair with the pyrimidine cytosine (C) within a second nucleic acid sequence. Thus, a base pairing between two strands (nucleic acid sequences) that does not follow and comply with such rules would be deemed a "mismatched" base pair, e.g., a pairing between G and U, A and G, A and C, G and T, G and U, and so on. A guide strand within the double stranded sequence of the stem-loop structures shown therein, which contain one or more "mismatched" base pairs relative to the passenger strand, creates a bulge in the double stranded stem sequence.

Accordingly, the bifunctional shRNAs may comprise shRNAs designed to enter into and interact with both cleavage-dependent RISC and cleavage-independent RISC. A higher level of gene "knock-down" is achieved using such bifunctional shRNAs compared to other currently-available RNAi methods and compositions, including siRNAs and conventional shRNAs (i.e., shRNA constructs designed to enter cleavage-dependent RISC or cleavage-independent RISC, but not both).

As used herein, gene "knock-down" refers to effective quantitative and durable inhibition of expression. Such gene "knock-down" may be manifested, and/or apparent, in the suppression of target gene mRNA translation, increased target cell apoptosis and/or cell kill.

As used herein, "target gene" refers to a nucleic acid sequence in a cell, wherein the expression of the sequence may be specifically and effectively modulated using the bifunctional shRNA. In certain embodiments, the target gene may be implicated in the growth (proliferation), maintenance (survival), and/or migratory (metastatic) behavior of an individual's cancer. The invention provides, however, that the target gene may be implicated in any other disease or medical condition, and is not limited to genes implicated in cancer. For example, the target gene may represent any sequence that an investigator or clinician wishes to silence (i.e., reduce the expression level of such target gene).

Vector sequence may comprise a promoter, which is operably linked (or connected), directly or indirectly, to a sequence encoding the bifunctional shRNAs. Such promoters may be selected based on the host cell and the effect sought. Non-limiting examples of suitable promoters include constitutive and inducible promoters, such as inducible RNA polymerase II (pol II)-based promoters. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case it will be appreciated that the T7 polymerase must also be present). The invention shall not be restricted to the use of any single promoter, especially since the invention may comprise two or more bifunctional-shRNAs (i.e., a combination of effectors), including but not limited to incorporated shRNA singlets. Each incorporated promoter may control one, or any combination of, the shRNA singlet components.

In certain embodiments, the promoter may be preferentially active in the targeted cells, e.g., it may be desirable to preferentially express the bifunctional shRNA molecules in tumor cells using a tumor cell-specific promoter. Introduction of such constructs into host cells may be effected under conditions whereby the two or more RNA molecules that are contained within the bifunctional shRNA precursor transcript initially reside within a single primary transcript, such that the separate RNA molecules (each comprising its own stem-loop structure) are subsequently excised from such precursor transcript by an endogenous ribonuclease. The invention further provides that splice donor and acceptor sequences may be strategically placed within the primary transcript sequence to promote splicesome-mediated nuclear processing. The resulting mature shRNAs may then induce degradation, and/or translation repression, of target gene mRNA transcripts produced in the cell. Alternatively, each precursor stem-loop structure may be produced as part of a separate transcript, in which case each shRNA-encoding sequence will preferably include its own promoter and transcription terminator sequences. Additionally, the bifunctional shRNA precursor transcript may reside within a single primary transcript, which, optionally, further comprises of one or more mRNA sequences that encode one or more functional mammalian proteins. For example, the one or more mRNA sequences may encode certain proteins that are known to bolster a patient's immune system, or otherwise provide some preventative and/or therapeutic effect that will operate in parallel with the bifunctional shRNA.

The stem-loop structures of the shRNA molecules described herein may be about 40 to 100 nucleotides long or, preferably, about 50 to 75 nucleotides long. The stem region may be about 19-45 nucleotides in length (or more), or more preferably about 20-30 nucleotides in length. The stem may comprise a perfectly complementary duplex (but for any 3' tail), however, bulges or interior loops may be present, and even preferred, on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. More particularly, the loop portion will preferably be 6-15 nucleotides in size.

As described herein, the stem regions of the bifunctional shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nim.nih.qov/BLAST). Expression level of multiple target genes may be modulated using the methods and bifunctional shRNAs described herein. For example, the invention provides that a first set of bifunctional shRNAs may be designed to include a sequence (a guide strand) that is designed to reduce the expression level of a first target gene, whereas a second set of bifunctional shRNAs may be designed to include a sequence (a guide strand) that is designed to reduce the expression level of a second target gene. The different sets of bifunctional shRNAs may be expressed and reside within the same, or separate, preliminary transcripts. In certain embodiments, such multiplex approach, i.e., the use of the bifunctional shRNAs described herein to modulate the expression level of two or more target genes, may have an enhanced therapeutic effect on a patient. For example, if a patient is provided with the bifunctional shRNAs described herein to treat, prevent, or ameliorate the effects of cancer, it may be desirable to provide the patient with two or more types of bifunctional shRNAs, which are designed to reduce the expression level of multiple genes that are implicated in the patient's cancer.

In certain embodiments, the invention further provides that the bifunctional shRNA sequences may comprise stem sequences of naturally occurring miRNAs (e.g., miR-30, C. elegans let-7 and/or lin-4). While the presence of a miR-30 loop, for example, may be desirable, the invention provides that variations of that structure may be tolerated, wherein loops may be used that are greater than 72%, preferably greater than 79%, more preferably greater than 86%, and most preferably, greater than 93% identical to, for example, the miR-30 sequence (determined using well-known computer programs such as the BESTFIT program (Wisconsin Sequence Analysis Package, Version 8 for Unix, Genetics Computer Group, University Research Park, 575 Science Drive, Madison, Wis. 53711)).

The precursor sequences (or constructs) encoding the bifunctional shRNAs may be introduced into host cells using any of a variety of techniques and delivery vehicles well-known in the art. For example, infection with a viral vector comprising one or more constructs may be carried out, wherein such viral vectors preferably include replication defective retroviral vectors, adenoviral vectors, adeno-associated vectors, lentiviral vectors, or measle vectors. In addition, transfection with a plasmid comprising one or more constructs may be employed. Such plasmids may be present as naked DNA, or may be present in association with, for example, a liposome (e.g., an immunoliposome). Still further, the delivery vehicle may consist of immunolipoplexes, targeted nanoparticles, targeted liposomes, cyclodextrins, nanoparticles, aptamers, dendrimers, chitosan, or pegylated derivatives thereof. The nature of the delivery vehicle may vary depending on the target host cell.

In-vivo delivery of the bifunctional shRNA-encoding constructs may be carried out using any one of a variety of techniques, depending on the target tissue. Delivery may be, for example, achieved by direct injection, inhalation, intravenous injection or other physical methods (including via micro-projectiles to target visible and accessible regions of tissue (e.g., with naked DNA). Administration may further be achieved via syringe needles, trocars, canulas, catheters, etc., as appropriate.

In addition to the methods of using the bifunctional shRNAs described herein, provided for are shRNAs themselves. Accordingly, additional aspects include nucleic acid sequences, which may comprise a single contiguous sequence or multiple distinct sequences that, individually or collectively, encode two or more RNA molecules. According to such embodiments, a first RNA molecule will comprise a double stranded sequence that includes a guide strand sequence that is complementary to a portion of an mRNA transcript encoded by a target gene, whereas a second RNA molecule comprises a second double stranded sequence that includes a second guide strand sequence that is partially complementary to a portion of such mRNA transcript. Preferably, the second guide strand sequence of the second RNA molecule comprises one or more bases that are mismatched with a nucleic acid sequence of the mRNA transcript encoded by the target gene. According to further aspects, expression vectors are provided which comprise the nucleic acid sequences, and may be used to carry out the methods, and express the bifunctional shRNAs, described herein.

Still further, methods of using the nucleic acid sequences and bifunctional shRNAs are described herein to prevent, treat and/or ameliorate the effects of one or more medical conditions, including without limitation various types of cancer. For example, the invention provides that the bifunctional shRNAs described herein may be used to reduce the expression level of one or more target genes that are implicated in cancer cell growth, survival, and/or metastasis. For example, as demonstrated in the Examples below, the bifunctional shRNAs may be used to reduce the expression level of certain target genes that encode scaffold proteins, which have been found to be over-expressed in cancer cells. Non-limiting examples of such target genes include Stathmin-1, RACK-1, Annexin II, and others.

The bifunctional shRNAs may further be used, for example, to reduce the expression level of pro-inflammatory genes or anti-apoptosis genes where therapeutically desirable. For example, expression of BCL-2 or acid ceramidase has been found to render tumor cells resistant to chemotherapy. Using the bifunctional shRNAs described herein, the expression level of BCL-2 or acid ceramidase may be reduced, thereby enhancing the ability of chemotherapeutic agents to cause tumor cells to undergo senescence. Similarly, T-cells isolated from a tumor-bearing patient can be modified ex-vivo using precursor sequences encoding bifunctional shRNAs designed to reduce the expression level of the TGF-.beta. receptor, thereby affecting the patient's immune response. Upon reintroduction into the patient, the killing ability of the T-cells will be enhanced. Likewise, T-cells can be modified ex-vivo to inhibit expression of the Fas receptor, thereby increasing the tumor killing capacity of the cells upon reintroduction.

It is further provided that target genes can be naturally occurring sequences, transgenes or can be pathogen sequences present, for example, as a result of infection. For example, the bifunctional shRNAs of the invention can be used to "turn off" papilloma viruses in humans (e.g., in the uterus by using an appropriately designed adeno-associated viral vector).

In addition to therapeutic applications, the bifunctional shRNAs described herein may be used in research-oriented applications. Cultured cells suitable as hosts for the precursor sequences encoding the bifunctional shRNAs of the present invention include both primary cells and cell lines. These cells may be human cells, including human stem cells, animal cells, plant cells, or other types of cells. A construct of the invention encoding the bifunctional shRNAs may be introduced into cultured cells to inactivate a specific gene of unknown function. Silencing the gene of interest using the bifunctional shRNAs can be used as an approach to assess its function. Bifunctional shRNAs may be introduced into non-human animal cells to produce a model experimental animal. In the case of experimental animals, the bifunctional shRNAs can be used for large-scale analysis of gene function.

Materials often used for Bi-functional shRNA design:
Computer with Internet access.
Other useful materials for construction of bi-shRNA:
1. DNA synthesis vendor or capacity.
2. Expression vectors.
3. Customized oliognucleotides
4. T4 DNA ligase.
5. Agarose gel electrophoresis.
6. DNA gel extraction kit.
7. Restriction enzymes
8. Competent *E. coli* cells.
9. Plasmid isolation kit
10. Thermal cycler Other useful materials to assess comparative knockdown by co-transfection.
1. Gene Pulser XCell Electroporation apparatus (Bio-Rad).
2. Gene Pulser Cuvettes (Bio-Rad)
3. Tissue culture cells.
4. Target gene expression vector.
5. For protein extraction and estimation.
CellLytic™-.M. Sigma Cat # C-2978
Protease Inhibitor Cocktail. Sigma Cat # P8340
Cell scrapers
Orbital Shaker
Microfuge (Refrigerated).
Coomassie Plus—Bradford™ Assay Kit/Pierce Cat.#23236
Pre diluted Protein Standards (Pierce-Cat #23208)
96 well round bottom plate
Multichannel pippet.
ELISA plate reader (Molecular Devises)
6. Materials required for or Western immunoblot:
Mini-Protein II Cell: Mini vertical electrophoresis system Bio-Rad Cat#195-2940
Mini-Protein II Ready Gels-12% Tris-Hcl, 10 wells
Running Buffer. (TGS Buffer) Bio-Rad Cat #161-0772
Precision Plus All Blue standards Bio-Rad Cat #161-0373
Lammellie Sample Loading Buffer.
β-Mercaptoethanol
Pre prepared cell lysate with known protein concentration.
Mini-Trans blot module (Bio-Rad Cat #170-3935)
Trans-blot PVDF membrane Sandwich (Bio-Rad cat #162-0219)
Transfer buffer (TG Buffer)
Methanol.
Stir plate.

Power Pack
DPBS (Invitrogen Cat#:14190-250)
Non-fat dried milk, for blocking non specific binding.
Tween-20
Primary Antibody to specific protein
Primary Antibody to loading control
HRP conjugated secondary antibody
SuperSignal West Dura Extended Duration Substrate (ThermoScientific, Pierce: Cat #34076
Orbital Shaker plate.
SYNGENE G:BOX
Material required for stem-loop RT-PCR for mature shRNA detection:
1. Thermal cycler.
2. Microcentrifuge.
3. SuperScript III RT (including reverse transcriptase, 5× first strand buffer, and 0.1M DTT).
4. RNase H.
5. dNTP mix, 10 mM.
6. RNaseOut (40 U/μl).
7. siRNA for positive control.
8. Stem-loop RT primer.
9. Stem-loop PCR primer.
10. mature shRNA specific PCR primers.
11. Total cellular RNA including small RNA and miRNA extracted using mirVana kit (Ambion, Tex.)
12. Agarose gel electrophoresis and TA cloning kit Materials required for 5' RLM-RACE for Cleavage Product Detection:
1. Thermal cycler
2. Microcentrifuge
3. Microcon YM-100 centrifugal filter
4. T4 RNA ligase and buffer
5. SuperScript III RT (including reverse transcriptase, 5× first strand buffer, and 0.1M DTT)
6. RNase H
7. dNTP mix (10 mM)
8. RNaseOut (40 U/μl).
9. Platinum Taq Kit (including Platinum Taq Polymerase, 5×PCR buffer and 10 mM MgCl$_2$)
10. RNA oligo:

(5'rCrGrArCrUrGrGrArGrCrArCrGrArGrGrArCrArCrUrGrAr
CrArUrGrArCrUrGrArArGrGrArGrUrArGrArArA3')

13. Gene specific RT primer and PCR primers
14. Total RNA isolated with the mirVana miRNA isolation kit or RNeasy Mini kit.
15. Agarose gel electrophoresis and DNA gel extraction kit.

Materials required for Preparation of DNA-DOTAP:Chol Lipoplexes:
1. Certified Biological Safety Cabinet (BSC) (The Baker Company).
2. Spectrophotometer with standard and turbidity cell holder (Beckman Coulter).
3. ZetaSizer Nano (Malvern).
4. Quartz semi-microcell cuvette (Beckman Coulter).
5. Vortexer (VWR).
6. Pipettors (Gilson) and Pipet tips (Phenix).
7. Acrodisc filter 0.2 μm (Pall).
8. GMP (GLP) Grade plasmid DNA (≥2.0 μg/μl in water).
9. 5× DOTAP:Cholesterol Liposomes (Gradalis).
10. Sterile water for irrigation (Baxter).
11. Sterile D5W (Baxter).
12. Ultra High Pure Argon gas (Airgas).
13. Septihol (USP 70% v/v Isopropyl Alcohol+USP 30% v/v Purified Water) (Steris).

Overview of an embodiment of methods to design a bi-shRNA:
1. Selecting target site sequences using available computer programs.
2. Performing a BLAST search to identify target sites with lowest homology hits to other mRNA of the targeted species.
3. Plugging the 19 nucleotides passenger strand (sense strand, blue boxed region on FIG. 2a) and guide strand (anti-sense strand, purple boxed region in FIG. 2(a) sequences into both stems of, e.g., the miR30a backbone sequence.
4. Exchanging nucleotides 9, 10, and 11 (counting from the 3' end of the passenger strand) of the second stem-loop structure with nucleotides mismatches to the guide strand.
5. Running both stem-loop structure on mfold program, the ΔG free energy of the hairpin with mismatches should fall between −10 Kcal.mole-1 and equilibrium.
6. If the ΔG free energy is beyond −10 Kcal.mole-1, additional mismatches should be introduced at the passenger strand of the second hairpin. The additional mismatch introduced is preferably at the 3' half of the passenger strand.

2.2. Overview of an embodiment of methods for construction of bi-shRNA expression vector:
1. Determining the target sequence of the bi-shRNA expression unit.
2. Designing overlapping DNA oligonucleotides from both strands with sticky ends for ligation. An overhang of at least four nucleotides should be sufficient. The upper limit of oligonucleotides length for DNA synthesis is about 50 nucleotides, thus DNA fragment should space evenly and less than 50 nucleotides each.
3. A 5' phosphate should be placed on each fragment for efficient ligation. The cloning site sequence can be built into the 5' and 3' end of the expression unit to expedite cloning into the expression vector.
4. Providing oligonucleotides by ordering or synthesizing oligonucleotides. Re-constitute synthesized oligonucleotides at 1 mg/ml.
5. Ligating the 5' fragments together with one-step ligation of equal amount of oligonucleotides each.
6. Ligating the 3' fragments together with one-step ligation of equal amount of oligonucleotides each.
7. Extracting and purifying the calculated full-length DNA fragments on agarose gel.
8. Ligating 5' fragment with linking fragment then 3' fragment and purifying the calculated full-length DNA fragment on agarose gel.
9. Ligating the purified fragment into expression vector and transforming competent E. coli cells.
10. Isolating colony, screening for clones with appropriate size insert.
11. Plasmids isolated from positive clones are further confirmed by sequencing.

Methods for comparing knockdown efficiency by co-transfection.
1. Determining the most effective electroporation condition and the most optimum amount of plasmid DNA for each cell types.
2. HEK-293 cells with electroporation condition recommended by Bio-Rad can be used.
3. Preparing DNA mix for electroporation with appropriate controls. It is essential to have a control with transgene expression vector and the empty vector for bi-shRNA expression, because promoter competition is often observed.
4. Transgene expression vector and bi-shRNA expression vector at 1:1 ratio can be used. In addition, a 1:2 ratio or 2:1 ratio, e.g., to validate the knockdown comparison in different doses can be used.
5. After electroporation, cells were plated at 40-50% confluency. Cells are removed at various time points to analyze comparative knockdown, the most effective time point is 48 hours post transfection.
6. Removing cells from the culture plate using Trypsin EDTA 0.25%. Washed in DPBS 2 times to remove any residual culture media containing serum. After the final wash cells are pelleted.
7. Preparing the lysis buffer by adding 1% of protease inhibitor cocktail to the CellLyticM lysis buffer. For each pellet of $1.0 \times 10^7$ cells 500 µl of the lysis buffer is added. Pipette up and down to mix cells with the lysis buffer. The lysis buffer plus the cell mixture should be cloudy but without being too dense. If the mixture is too dense another 100 to 200 µl of lysis buffer is added. Incubate at room temperature for 30 minutes on a slow shaker. Centrifuge the lysed cells for 20 minutes at 12,000-20,000×g to pellet the cellular debris. Remove the protein containing supernatant to a chilled tube.
8. Protein estimation is done by Coomassie Bradford Plus Assay.
9. Equal amount of total protein is loaded onto Ready Gel for PAGE for Western analysis.
10. Protein from the Gel is transferred to PVDF membrane.
11. Immuno probing is done with gene specific antibody and antibody to loading control protein.
12. HRP Conjugated Secondary antibody is used followed by Super Signal Dura Extended Duration Substrate to detect the signal.
13. Images are captured using G-Box and the band densities are quantified.
14. Side-by-side knockdown comparison of different bi-shRNA can be scored by semi-quantitative scan.

Demonstrating bi-shRNA expression by stem-loop RT-PCR.
1. Designing primers:
1.1 Design stem-loop RT primers for either passenger strand or guide strand according to the predicted mature shRNA sequence.
1.2 Design guide strand and passenger strand specific PCR primers according to the predicted mature shRNA sequence.
2. Reverse Transcription:
2.1. Add the following reagents to the tube containing 3.0 µg total RNA including miRNA: 1 ul stem-loop RT primer (10 µM), 1 µl 10 mM dNTP mix (Invitrogen).
2.2. Incubate the mixture for 5 minutes at 65° C. to disrupt RNA secondary structure.
2.3. Keep on ice for 2 minutes and centrifuge briefly.
2.4. Add the following reagents to the mixture above and bring the volume to 20 µl by adding nuclease-free water: 4 µl 5× first strand buffer, 1 µl 0.1 M DTT, 1 µl RNaseOut (40 U/µl), 1 µl Superscript III RT (200 µ/µl).
2.5. Mix well and incubate at 55° C. for 50 minutes.
2.6. Inactivate the RT reaction by incubating at 70° C. for 15 minutes.
2.7. Chill on ice for 2 minutes.
2.8. Add 1 µl RNase H to the reaction mix and incubate at 37° C. for 20 minutes. Centrifuge briefly and keep on ice or store in the −20° C. freezer.

PCR Setup: Make the master mix and follow the PCR parameters as below:

| REAGENT | VOLUME(µL) |
|---|---|
| Nuclease-free water | 32.6 |
| 5x PCR buffer | 10 |
| 25 mM MgCl2 | 3 |
| 10 nM dNTP | 1 |
| Stem-loop PCR primer | 1 |
| mature shRNA specific PCR primer. | 1 |
| GoTaq HotStart | 0.4 |
| cDNA | 1 |
| Total volume | 50 |

| CONDITIONS | | |
|---|---|---|
| 94° C. | 2 minutes | |
| 94° C. | 1 minutes | 35 cycles |
| 55° C. | 30 seconds | |
| 72° C. | 1 minutes | |
| 72° C. | 9 minutes | |
| 4° C. | hold | |

PCR Product Analysis: After the PCR amplification is completed, run a 20 µl of sample on a 4% agarose gel to visualize the amplicon. The predicted PCR amplicon is TA cloned and then sequenced.

Demonstrating Target gene cleavage by 5' RLM-RACE:
1. Ligating RNA oligo to RNA molecules with exposed 5' phosphate: Add 1-3 µg of total RNA from each sample to 250 ng of RNA oligo and mix well by pipetting several times
2. Incubate the mixture at 65° C. for 5 minutes in a thermal cycler and then hold at 4° C. for 2 minutes.
3. Add the following reagents to the tube, mix well, and centrifuge briefly: 2 ul of 10× ligase buffer, 2 µl of RNaseOut (40 U/µl), 2 µl of nuclease-free water, and 1 µl of T4 RNA ligase (10 U/µl). Incubate the mixture at 37° C. for 1 hour in a thermal cycler.
4. RNA Purification: After 37° C. incubation, add 80 µl of nuclease-free water to the 20 µl ligation product, and load the 100 µl mixture into a microcon YM-100 centrifugal filter. Centrifuge at 500×g for 15 minutes. Turn the column upside down in a new tube and centrifuge at 1000×g for 3 minutes. The elution is about 10 µl.
5. Reverse Transcription (RT): Add the following reagents to the tube containing 10 µl of ligated RNA from above: 1 ul of gene-specific RT primer, 1 µl of dNTP mix, and 1 ul of nuclease-free water. Incubate the mixture for 5 minutes at 65° C., and then keep on ice for 1 minute. Add the following reagents to the mixture of ligated RNA and RT primer: 4 µl of 5× first strand buffer, 1 µl of 0.1M DTT, 1 µl of RNaseOut, and 1 µl of SuperScript III RT. Incubate at 55° C. for 50 minutes, followed by incubating at 70° C. for 15 minutes. Add 1 µl of RNaseH to the reaction mix and incubate at 37° C. for 20 minutes
6. Amplifying cDNA ends (1st PCR, touch-down): Set up the reaction mix as listed below:

| Reagent | Volume(µl) |
|---|---|
| nuclease-free water | 36.5 |
| 5x PCR buffer | 5 |
| 25 mM MgCl$_2$ | 2 |

-continued

| Reagent | Volume(μl) |
|---|---|
| 10 mM dNTP | 1 |
| Generacer 5' Primer | 3 |
| GSP primer | 1 |
| Platinum Taq | 0.5 |
| cDNA | 1.0 |
| Total volume | 50 |

Performing touch-down PCR following the parameters in the table below:

| CONDITIONS | | |
|---|---|---|
| 94° C. | 2 minutes | |
| 94° C. | 30 seconds | 5 cycles |
| 72° C. | 1 minute | |
| 94° C. | 30 seconds | 5 cycles |
| 70° C. | 1 minute | |
| 94° C. | 1 minute | 25 cycles |
| 65° C. | 30 seconds | |
| 72° C. | 1 minute | |
| 72° C. | 10 minutes | |
| 4° C. | hold | |

Nested-PCR (2nd PCR): Nested PCR is employed to increase the specificity and sensitivity of the RACE product amplification. The reaction master mix is set up as listed below:

| Reagent | Volume(μl) |
|---|---|
| nuclease-free water | 38.5 |
| 5x PCR buffer | 5 |
| 25 mM MgCl2 | 2 |
| 10 mM dNTP | 1 |
| Generacer 5' nested primer | 1 |
| GSP nested primer | 1 |
| Platinum Taq | 0.5 |
| DNA template from 1$^{st}$ PCR | 1 |
| Total volume | 50 |

The PCR is performed following the parameters in the table below:

| CONDITIONS | | |
|---|---|---|
| 94° C. | 2 minutes | |
| 94° C. | 30 seconds | 25 cycles |
| 65° C. | 30 seconds | |
| 72° C. | 1 minute | |
| 72° C. | 10 minutes | |
| 4° C. | hold | |

Agarose gel electrophoresis and sequencing: 20 μl of the nested-PCR product is separated on a 2% agarose gel. The image of the agarose gel is captured by a imaging system. The identity of the PCR product is further confirmed by sequencing.

Preparation of DNA-DOTAP:Chol Lipoplexes.

1. Perform formulation in BSC. Do a test run before doing bulk manufacture run.
2. Bring the liposomes, plasmid DNA, D5W, and water to room temperature.
3. Transfer D5W into 50 ml conical tubes using a 60 ml syringe and 16 G needle.
4. Measure the plasmid DNA concentration in a spectrophotometer by OD260 using a standard cuvette holder.
5. In a 1.5 ml tube, dilute plasmid DNA to 1.0 μg/μl with D5W.
6. In a 1.5 ml tube, combine 3 volumes of D5W and 2 volumes of 5×DOTAP:Chol stock, mix to make 2× liposomes.
7. Prepare the Lipoplex by transfering the diluted DNA (1.0 μg/μl) into an equal volume of 2× liposomes and mix by pipetting up and down.
8. Check for any signs of precipitation. If no precipitation is visible, proceed to next step. If precipitation is visible, repeat Steps 5-7 using less DNA and note the change.
9. Spectrophotometric Analysis: Change the cuvette holder to the turbidity cell holder. Dilute the DNA-Lipoplex 20 fold with sterile water. Blank the spectrophotometer at 400 nm with sterile water and then measure the OD400 of the diluted DNA-Lipoplex. Acceptable range is 0.65-0.95. If the OD400 reading is too high, repeat Steps 5-7 using less DNA and note the changes in the operator comments section. If the OD400 reading is too low, repeat Steps 5-7 using more DNA and note the changes.
10. After the test run is within the acceptable range, the same process is repeated to complete the manufacture run. Combine all DNA-Lipoplexes, mix and measure the OD400 of the final pooled product. Vial aliquot samples for quality control studies and bottle the remainder lipoplex. Layer argon gas (filtered through a 0.2 μm acrodisc filter) into each vial to displace the ambient air and seal the lid.
11. Quality control tests include particle analysis, USP sterility, LAL endotoxin assay, residual chloroform analysis by GC/MS, and thin layer chromatography to identify lipids (QC tests service companies are listed below).
12. Particle Analysis (size and zeta potential): Rinse the folded capillary cell with 5 ml 100% ethanol, and then with 5 ml USP water. Load 20 fold diluted DNA-Lipoplex sample into the capillary cell. Measure the average particle size (acceptable range <500 nm) and zeta potential (acceptable range >40 mV).

Sterility and Endotoxin Service Provider: AppTec, 1265-B Kennestone Circle, Marietta, Ga. 30066. Residual Chloroform Service Provider: Exova Inc., 9240 Santa Fe Springs Rd, Santa Fe Springs, Calif. 90670. Lipid Analysis Service Provider: Avanti Polar Lipids, Inc., 700 Industrial Park Drive.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Fire A Z Gene silencing by double-stranded RNA (Nobel Lecture). Angewandte Chemie (International ed 2007; 46: 6966-6984.
2. Mello C C, Return to the RNAi world: rethinking gene expression and evolution. Cell death and differentiation 2007; 14: 2013-2020.
3. Burnett J C, Rossi J J and Tiemann K, Current progress of siRNA/shRNA therapeutics in clinical trials. Biotechnology journal 2011; 6: 1130-1146.
4. Davidson B L and McCray P B, Jr. Current prospects for RNA interference-based therapies. Nature reviews 2011; 12: 329-340.
5. Wang Z, Rao D D, Senzer N and Nemunaitis J RNA Interference and Cancer Therapy. Pharmaceutical research 2011; 2011 Oct. 19 [Epub ahead of print].
6. Phalon C, Rao D D and Nemunaitis J Potential use of RNA interference in cancer therapy. Expert reviews in molecular medicine 2010; 12: e26.
7. Drews J Genomic sciences and the medicine of tomorrow. Nature biotechnology 1996; 14: 1516-1518.
8. Drews J Drug discovery: a historical perspective. Science 2000; 287: 1960-1964.
9. Verdine G L and Walensky L D The challenge of drugging undruggable targets in cancer: lessons learned from targeting BCL-2 family members. Clin Cancer Res 2007; 13: 7264-7270.
10. Matranga C, Tomari Y, Shin C, Bartel D P and Zamore P D Passenger-strand cleavage facilitates assembly of siRNA into Ago2-containing RNAi enzyme complexes. Cell 2005; 123: 607-620.
11. Preall J B and Sontheimer E J RNAi: RISC gets loaded. Cell 2005; 123: 543-545.
12. Parker J S and Barford D Argonaute: A scaffold for the function of short regulatory RNAs. Trends Biochem Sci 2006; 31: 622-630.
13. Gregory R I, Chendrimada T P, Cooch N and Shiekhattar R Human RISC couples microRNA biogenesis and post-transcriptional gene silencing. Cell 2005; 123: 631-640.
14. Tang G siRNA and miRNA: an insight into RISCs. Trends Biochem Sci 2005; 30: 106-114.
15. Grimson A, Farh K K, Johnston W K, Garrett-Engele P, Lim L P and Bartel D P MicroRNA targeting specificity in mammals: determinants beyond seed pairing. Molecular cell 2007; 27: 91-105.
16. Ameres S L, Martinez J and Schroeder R Molecular basis for target RNA recognition and cleavage by human RISC. Cell 2007; 130: 101-112.
17. Parker J S, Roe S M and Barford D Molecular mechanism of target RNA transcript recognition by Argonaute-guide complexes. Cold Spring Harbor symposia on quantitative biology 2006; 71: 45-50.
18. Rao D D, Vorhies J S, Senzer N and Nemunaitis J, siRNA vs. shRNA: similarities and differences. Adv Drug Deliv Rev 2009; 61: 746-759.
19. Kim D H, Behlke M A, Rose S D, Chang M S, Choi S and Rossi J J, Synthetic dsRNA Dicer substrates enhance RNAi potency and efficacy. Nature biotechnology 2005; 23: 222-226.
20. McAnuff M A, Rettig G Rand Rice K G, Potency of siRNA versus shRNA mediated knockdown in vivo. J Pharm Sci 2007; 96: 2922-2930.
21. Rao D D, Maples P B, Senzer N et al., Enhanced target gene knockdown by a bifunctional shRNA: a novel approach of RNA interference. Cancer gene therapy 2010; 17: 780-791.
22. Templeton N S, Lasic D D, Frederik P M, Strey H H, Roberts D D and Pavlakis G N, Improved DNA: liposome complexes for increased systemic delivery and gene expression. Nature biotechnology 1997; 15: 647-652.
23. Chapman B S, Thayer R M, Vincent K A and Haigwood N L, Effect of intron A from human cytomegalovirus (Towne) immediate-early gene on heterologous expression in mammalian cells. Nucleic acids research 1991; 19: 3979-3986.
24. Simari R D, Yang Z Y, Ling X et al. Requirements for enhanced transgene expression by untranslated sequences from the human cytomegalovirus immediate-early gene. Molecular medicine (Cambridge, Mass 1998; 4: 700-706.
25. Grimm D, Streetz K L, Jopling C L et al. Fatality in mice due to oversaturation of cellular microRNA/short hairpin RNA pathways. Nature 2006; 441: 537-541.

26. Giering J C, Grimm D, Storm T A and Kay M A Expression of shRNA from a tissue-specific pol II promoter is an effective and safe RNAi therapeutic. Mol Ther 2008; 16: 1630-1636.

27. Walton S P, Wu M, Gredell J A and Chan C Designing highly active siRNAs for therapeutic applications. The FEBS journal 2010; 277: 4806-4813.

28. Hofacker I L and Tafer H Designing optimal siRNA based on target site accessibility. Methods Mol Biol 2010; 623: 137-154.

29. Moore C B, Guthrie E H, Huang M T and Taxman D J, Short hairpin RNA (shRNA): design, delivery, and assessment of gene knockdown. Methods Mol Biol 2010; 629: 141-158.

30. Dawson L A and Usmani B A, Design, manufacture, and assay of the efficacy of siRNAs for gene silencing. Methods Mol Biol 2008; 439: 403-419.

31. Zeng Y and Cullen B R, Recognition and cleavage of primary microRNA transcripts. Methods Mol Biol 2006; 342: 49-56.

32. Siolas D, Lerner C, Burchard J et al., Synthetic shRNAs as potent RNAi triggers. Nature biotechnology 2005; 23: 227-231.

33. Barteau B, Chevre R, Letrou-Bonneval E, Labas R, Lambert O and Pitard B, Physicochemical parameters of non-viral vectors that govern transfection efficiency. Curr Gene Ther 2008; 8: 313-323.

34. Chesnoy S and Huang L, Structure and function of lipid-DNA complexes for gene delivery. Annual review of biophysics and biomolecular structure 2000; 29: 27-47.

35. Templeton N S, Liposomes for gene transfer in cancer therapy. Methods Mol Biol 2010; 651: 271-278.

36. Phadke A P, Jay C M, Wang Z et al. In vivo safety and antitumor efficacy of bifunctional small hairpin RNAs specific for the human Stathmin 1 oncoprotein. DNA Cell Biol 2011; 30: 715-726.

37. Nemunaitis G, Jay C M, Maples P B et al., Hereditary Inclusion Body Myopathy: Single Patient Response to Intravenous Dosing of GNE Gene Lipoplex. Human gene therapy 2011; 2011 Apr. 25 [Epub ahead of print].

38. Firozi P, Zhang W, Chen L, Quiocho F A, Worley K C and Templeton N S, Identification and removal of colanic acid from plasmid DNA preparations: implications for gene therapy. Gene therapy 2010; 17: 1484-1499.

What is claimed is:

1. A method for designing a bi-shRNA expression cassette encoding a bi-shRNA comprising:
   selecting one or more first target site sequences of a targeted species, wherein the one or more first target site sequences have low homology with other mRNAs of the targeted species, wherein low homology is selected from the group consisting of less than 75%, less than 80%, less than 90%, less than 95%, and less than 98% homology;
   selecting one or more second target site sequences of a targeted species, wherein the one or more first target site sequences have low homology with other mRNAs of the targeted species, wherein low homology is selected from the group consisting of less than 75%, less than 80%, less than 90%, less than 95%, and less than 98% homology;
   providing a backbone sequence comprising a first and a second stem-loop structure, wherein the first stem-loop structure comprises two first insertion sites linked by a first loop sequence within the first stem and wherein the second stem-loop structure comprises two second insertion sites linked by a second loop sequence within the second stem; wherein the first and the second stem-loop structures are linked by a sequence longer than 5 nucleotides;
   inserting a first passenger strand and a first guide strand into the two first insertion sites to form the first stem, wherein the first passenger strand is homologous to the one or more first target site sequences and wherein the first guide strand is complementary to the first passenger strand, or wherein the first passenger strand is identical to the reverse orientation of the first guide strand; and
   inserting a second passenger strand and a second guide strand into the two second insertion sites to form the second stem-loop structure, wherein either the second passenger strand or the second guide strand is homologous with the one or more first target site sequences, or wherein either the second passenger strand or the second guide strand is homologous with the one or more second target sites sequences, wherein the second passenger strand and the second guide strand are partially complementary, wherein partially complementary is defined has having 1, 1-2, 1-3, 1-4, 1-5, 1-6, 1-7, 1-8, 1-9, or 1-10 nucleotide mismatches when paired.

2. The method of claim 1, wherein the first stem-loop structure and the second stem-loop structure each comprise a loop of 6-15 nucleotides in size.

3. The method of claim 1, wherein the first stem-loop structure and the second stem-loop structure are each 40 to 100 nucleotides long.

4. The method of claim 1, wherein the first stem-loop structure and the second stem-loop structure are each 50 to 75 nucleotides long.

5. The method of claim 1, wherein the first stem-loop structure and the second stem-loop structure each comprise a stem of 19-45 nucleotides in size.

6. The method of claim 1, wherein the first stem-loop structure and the second stem-loop structure each comprise a stem of 20-30 nucleotides in size.

7. The method of claim 1, wherein at least one passenger strand and one guide strand are 16-19 nucleotides long.

8. The method of claim 1, wherein at least one passenger strand and one guide strand are 19-22 nucleotides long.

9. The method of claim 1, wherein the first loop and the second loop are identical.

10. The method of claim 1, wherein the first loop encodes the sequence AGUGAAGCCACAGAUGU (SEQ ID NO.:1).

11. The method of claim 1, wherein the backbone sequence comprises the following sequence upstream of the second passenger strand and within the second stem: GCUGUUGACAGUGAGCGCC (SEQ ID NO.:5); and wherein the backbone sequence comprises the following sequence downstream of the second guide strand and within the second stem: GUUGCCUACUGCCUCGGAAGC (SEQ ID NO.:6).

12. The method of claim 1, wherein the one or more nucleotide mismatches are located at nucleotide position 9, 10, and 11.

13. The method of claim 1, further comprising determining a ΔG free energy of the second stem loop structure and introducing additional mismatches at the 3' half of the second passenger strand if ΔG free energy is beyond about $-10 \text{Kcal} \cdot \text{mole}^{-1}$.

14. The method of claim 1, wherein the bi-shRNA expression cassette further comprises a lead transcript upstream of the stem-loop structures.

15. The method of claim 1, further comprising
designing at least three bi-shRNA expression cassettes for the same gene; and
comparing knockdown efficiency of the at least three bi-shRNA expression cassettes by in vitro assessment.

16. The method of claim 1, further comprising operably linking the bi-shRNA expression cassette to a promoter, wherein the first stem-loop structure is upstream in relation to the second stem loop structure.

17. The method of claim 1, further comprising integrating the bi-shRNA expression cassette into genomic DNA, wherein the genomic DNA is human DNA.

18. The method of claim 1, further comprising inserting the bi-shRNA expression cassette into an expression vector.

19. The method of claim 14, wherein the expression vector comprises a 5'UTR and an intron.

20. The method of claim 14, wherein the expression vector comprises a RNA polymerase II promoter operably linked to the expression of the bi-shRNA expression cassette.

21. The method of claim 1, wherein the backbone sequence comprises a miR30a backbone sequence.

22. The method of claim 1, wherein selecting one or more target site sequences comprises searching by BLAST to find target sites with lowest homology hits to other mRNA of the targeted species.

23. The method of claim 1, wherein providing for synthesis is selected from the group comprising assembling multiple overlapping DNA oligonucleotides, synthesizing a polynucleotide, and combinations thereof.

24. The method of claim 1, wherein providing for synthesis comprises designing DNA oligonucleotides from both strands having an overlap, wherein the overlap is at least four nucleotides.

25. The method of claim 1, further comprising preparing a DNA-DOTAP:Chol Lipoplex.

26. The method of claim 1, wherein the one or more first target site sequences and the one or more second target site sequence are not identical and located within the same gene of the targeted species.

27. The method of claim 1, further comprising transcribing the bi-shRNA expression cassette.

28. The method of claim 27, wherein the bi-shRNA expression cassette is integrated into genomic DNA.

29. The method of claim 1, further comprising integrating the bi-shRNA expression cassette into a crop genomic DNA, wherein crop is a non-animal species or variety that is grown to be harvested as food, livestock fodder, fuel or for any other economic purpose.

30. The method of claim 1, further comprising the step of providing for synthesis of the bi-shRNA expression cassette.

31. The method of claim 1, wherein the targeted species comprises a human nucleic acid sequence.

* * * * *